US011109736B2

(12) United States Patent
Gaus et al.

(10) Patent No.: US 11,109,736 B2
(45) Date of Patent: Sep. 7, 2021

(54) METHOD AND CLEANING DEVICE FOR CLEANING ITEMS TO BE CLEANED

(71) Applicant: MEIKO Maschinenbau GmbH & Co. KG, Offenburg (DE)

(72) Inventors: Bruno Gaus, Offenburg (DE); Thomas Näger, Offenburg (DE); Thomas Peukert, Bühl (DE); Allen Jakway, Zell am Harmersbach (DE); Pamela Kasper, Willstätt (DE); Werner Röderer, Friesenheim (DE)

(73) Assignee: MEIKO MASCHINENBAU GMBH & CO. KG, Offenburg (DE)

( * ) Notice: Subject to any disclaimer, the term of this patent is extended or adjusted under 35 U.S.C. 154(b) by 51 days.

(21) Appl. No.: 16/410,618

(22) Filed: May 13, 2019

(65) Prior Publication Data
US 2019/0261828 A1 Aug. 29, 2019

Related U.S. Application Data

(63) Continuation of application No. PCT/EP2017/079020, filed on Nov. 13, 2017.

(30) Foreign Application Priority Data

Nov. 14, 2016 (DE) ..................... 10 2016 222 308.9

(51) Int. Cl.
*A47L 15/00* (2006.01)
*A47L 15/24* (2006.01)
(Continued)

(52) U.S. Cl.
CPC ....... *A47L 15/0055* (2013.01); *A47L 15/0049* (2013.01); *A47L 15/241* (2013.01);
(Continued)

(58) Field of Classification Search
CPC ............... A47L 15/0055; A47L 15/241; A47L 15/4287; A47L 15/4289; A47L 15/46;
(Continued)

(56) References Cited

U.S. PATENT DOCUMENTS

| 3,896,827 A | 7/1975 | Robinson |
| 4,439,242 A | 3/1984 | Hadden |

(Continued)

FOREIGN PATENT DOCUMENTS

| DE | 10 2004 049 392 A1 | 4/2006 |
| DE | 10 2006 014 464 B3 | 10/2007 |

(Continued)

OTHER PUBLICATIONS

English Translation of International Preliminary Report on Patentability, PCT/EP2017/079020, dated Oct. 19, 2018, 6 pages.

(Continued)

*Primary Examiner* — Sharidan Carrillo
(74) *Attorney, Agent, or Firm* — Bose McKinney & Evans LLP

(57) ABSTRACT

A method for cleaning items to be cleaned is disclosed. A cleaning device is used that has at least one cleaning chamber and at least one applicator for applying at least one cleaning fluid to the items to be cleaned in the cleaning chamber. A desired hygiene value is prespecified. The method further includes time-resolved recording of at least two influencing variables which influence hygienization of the items to be cleaned. Hygiene share values are determined from the influencing variables using a prespecified relationship between each influencing variable and the respective hygiene value share of said influencing variable. An expected actual hygiene value at the end of the cleaning from the hygiene value shares is ascertained and compared with the desired hygiene value. At least one of the influencing variables is changed based on the comparison. An inventive cleaning device is also disclosed.

16 Claims, 3 Drawing Sheets

(51) Int. Cl.
  *A47L 15/42* (2006.01)
  *A47L 15/46* (2006.01)
  *B08B 3/02* (2006.01)
  *B08B 3/08* (2006.01)
  *B08B 3/10* (2006.01)
  *A61L 2/18* (2006.01)
  *A61L 2/07* (2006.01)
  *A61G 9/02* (2006.01)

(52) U.S. Cl.
  CPC ....... *A47L 15/4287* (2013.01); *A47L 15/4289* (2013.01); *A47L 15/46* (2013.01); *A61L 2/18* (2013.01); *B08B 3/02* (2013.01); *B08B 3/08* (2013.01); *B08B 3/10* (2013.01); *A47L 15/0076* (2013.01); *A47L 2401/023* (2013.01); *A47L 2401/11* (2013.01); *A47L 2401/12* (2013.01); *A47L 2401/14* (2013.01); *A47L 2401/20* (2013.01); *A47L 2401/34* (2013.01); *A47L 2501/04* (2013.01); *A47L 2501/05* (2013.01); *A47L 2501/06* (2013.01); *A47L 2501/07* (2013.01); *A47L 2501/20* (2013.01); *A47L 2501/24* (2013.01); *A47L 2501/30* (2013.01); *A61G 9/02* (2013.01); *A61L 2/07* (2013.01); *A61L 2202/17* (2013.01); *B08B 2203/007* (2013.01); *B08B 2203/0217* (2013.01)

(58) Field of Classification Search
  CPC ............. A47L 2401/12; A47L 2401/14; A47L 2401/28; A47L 2401/10; B08B 3/02; B08B 2/08; B08B 3/10; B08B 2203/007; B08B 2203/0217
  See application file for complete search history.

(56) References Cited

U.S. PATENT DOCUMENTS

| | | | |
|---|---|---|---|
| 5,603,233 A | | 2/1997 | Erickson et al. |
| 5,820,691 A | | 10/1998 | Hartman |
| 6,302,968 B1 | * | 10/2001 | Baum ................ C11D 3/2079 134/30 |
| 6,615,850 B1 | | 9/2003 | Hornung |
| 2007/0246071 A1 | | 10/2007 | Streb |
| 2008/0077281 A1 | | 3/2008 | Gaus |
| 2008/0115807 A1 | | 5/2008 | Gaus |
| 2008/0283096 A1 | | 11/2008 | Scheringer et al. |
| 2009/0183753 A1 | | 7/2009 | Maennle et al. |
| 2010/0114132 A1 | * | 5/2010 | Piccionelli ............ A61F 5/0059 606/157 |
| 2010/0132735 A1 | | 6/2010 | Gaus et al. |
| 2010/0263687 A1 | | 10/2010 | Braun et al. |
| 2011/0056520 A1 | | 3/2011 | Varacins et al. |
| 2011/0203616 A1 | * | 8/2011 | Berner ................ A47L 15/0047 134/25.2 |
| 2011/0209729 A1 | * | 9/2011 | Beaudet ............ A47L 15/0021 134/18 |
| 2014/0034088 A1 | | 2/2014 | Padtberg et al. |
| 2015/0173587 A1 | | 6/2015 | Firchau et al. |
| 2016/0220089 A1 | | 8/2016 | Peukert et al. |
| 2016/0309981 A1 | | 10/2016 | Dirschus et al. |
| 2017/0065146 A1 | | 3/2017 | Himmelsbach et al. |
| 2019/0261828 A1 | * | 8/2019 | Gaus .................. A47L 15/4287 |

FOREIGN PATENT DOCUMENTS

| | | |
|---|---|---|
| DE | 10 2006 019 546 A1 | 12/2007 |
| DE | 10 2007 021 245 A1 | 11/2008 |
| DE | 10 2008 024 543 A1 | 11/2009 |
| DE | 10 2009 024 569 A1 | 4/2011 |
| DE | 10 2011 007 507 A1 | 10/2012 |
| DE | 10 2012 213 271 A1 | 1/2014 |
| DE | 10 2013 203 933 A1 | 9/2014 |
| DE | 10 2013 226 637 A1 | 6/2015 |
| DE | 10 2014 102 970 A1 | 9/2015 |
| EP | 1 886 615 A1 | 2/2008 |
| EP | 2 241 240 A1 | 10/2010 |
| EP | 2 053 959 B1 | 5/2013 |
| JP | 2000-083887 A | 3/2000 |
| JP | 2004-167164 A | 6/2004 |
| WO | WO 2006/097294 A1 | 9/2006 |
| WO | WO 2011/062790 A2 | 5/2011 |
| WO | WO-2015049228 A1 * | 4/2015 ............ H04W 84/10 |

OTHER PUBLICATIONS

English Translation of the International Search Report, PCT/EP2017/079020, dated Mar. 8, 2018, 2 pages.

NSF International Standard/American National Standard for Food Equipment (NSF/ANSI Mar. 2010), Commercial Warewashing Equipment, Nov. 2, 2010, 41 pages.

Nicolella et al., Thermal Sanitizing in a Commercial Dishwashing Machine, Journal of Food Safety 31, 2011, pp. 81-90.

DIN EN ISO 15883-1, Washer-Disinfectors—Part 1: General Requirements, Terms, Definitions and Tests (ISO 15883-1:2006), Sep. 2009, 89 pages.

Commercial Dishwashing & Dishwashers, Arbeitsgemeinschaft Gewerbliches Geschirrspülen, Jan. 2008, Hagen, Germany, 9 pages.

Commercial Dishwashing and Environment, Arbeitsgemeinschaft Gewerbliches Geschirrspülen, Apr. 21, 2004, Hagen, Germany, 15 pages.

Commercial Dishwashing and Water, Arbeitsgemeinschaft Gewerbliches Geschirrspülen, Jan. 2008, Hagen, Germany, 7 pages.

Commercial Dishwashing and Terms, Arbeitsgemeinschaft Gewerbliches Geschirrspülen, Jan. 2008, Hagen, Germany, 18 pages.

Commercial Dishwashing & Hygiene, Arbeitsgemeinschaft Gewerbliches Geschirrspüllen, Mar. 2006, Hagen, Germany, 14 pages.

Commercial Dishwashing & Detergent, Arbeitsgemeinschaft Gewerbliches Geschirrspülen, May 22, 2007, Hagen, Germany, 5 pages.

Commercial Dishwashing & Dosing, Arbeitsgemeinschaft Gewerbliches Geschirrspüllen, Mar. 2007, Hagen Germany, 6 pages.

Practical Handbook of Commercial Dishwashing, Chapter 11 Version 1, Arbeitskreis Gewerbliches Geschirrspüllen, Apr. 2016, 26 pages.

Houben, Final Report on the IGF Project "Development of a Biocatalytic Color Indicator System for Process Control of Disinfection in Commercial Dishwashers," The Research Center, wfk—Cleaning Technology Institute, May 27, 2015, 73 pages.

Kasper, Evaluation of Various Germ-Reducing Influences in Rinsing Liquids of Industrial Dishwashers, 2014, 18 pages.

German Society for Hospital Hygiene, 12th Congress for Hospital Hygiene in Cooperation with the Eurpean Network to Promote Infection Prevention for Patient Safety, Berlin Russian House, Mar. 30 to Apr. 2, 2014, 52 pages.

DIN 10510, Commercial Dishwashing with Multi-Tank Transport Dishwashers—Hygiene Requirements and Procedure Testing, Apr. 2001, 30 pages.

DIN 10511, Commercial Glass Rinsing with Glasswashers—Hygienic Requirements, Examination, May 1999, 20 pages.

Michaels, Hospital Hygiene and Infection Prevention, ISSN 0720-3373, Jun. 2004, 26 Issue 3, 5 pages.

Kasper et al., From Vision to Reality! New Dimensions of the Hygiene Safety with the Lowest Use of Resources, 47th International Detergency Conference, May 20, 2015, 11 pages.

\* cited by examiner

METHOD AND CLEANING DEVICE FOR CLEANING ITEMS TO BE CLEANED

RELATED APPLICATIONS

This application is a continuation of PCT/EP2017/079020, filed Nov. 13, 2017, which claims priority to DE 10 2016 222 308.9, filed Nov. 14, 2016, the entire disclosures of which are incorporated herein by reference in their entirety.

BACKGROUND

This disclosure relates to a method and a cleaning device for cleaning items to be cleaned, in particular for use in commercial dishwashing and/or in large-scale kitchens. Cleaning devices of said kind can be used, for example, in facilities for mass catering, such as, in particular, office canteens, canteens in schools, public authorities, hospitals or care facilities. The cleaning device can be used, in particular, for cleaning items to be cleaned in the form of washware which are used directly or indirectly for preparing, storing or serving food and drinks. Said items to be cleaned may be, in particular, dishes and/or trays. Other fields of use of this disclosure are also feasible in principle, in particular fields of use with, in principle, any desired washware.

A large number of cleaning devices, also called cleaning appliances, which can clean and/or disinfect items to be cleaned are known from the prior art. In the text which follows, without restricting other possible fields of use, this disclosure makes reference largely to the field of commercial washing, for example commercial dishwashing. Therefore, in addition to automatic programmed washers with static washing processes, conveyor washers or pass-through washers in which the items to be cleaned are transported through one or more cleaning chambers by means of a transportation device are known for example. The design of these cleaning devices depends overall to a great extent on the various boundary conditions, such as the type of items to be cleaned, the degrees of soiling, the throughput or similar conditions for example. By way of example, reference can be made to cleaning devices which are described, for example, in DE 10 2004 056 052 A1, in DE 10 2007 025 263 A1 or in DE 10 2013 220 035 A1.

In contrast to domestic dishwashing, commercial washers generally have a plurality of fluid tanks in order to be able to accelerate a throughput of items to be cleaned. For example, in addition to the actual wash tank, a rinse tank is provided, in which rinse tank the temperature of a rinse or final rinse fluid can be adjusted as early as while the main washing process is still running. Conveyor washers generally have a large number of cleaning zones in which the items to be cleaned are sequentially cleaned. However, this increase in throughput is generally associated with a considerable increase in expenditure of energy and in many cases also an increase in a requirement for detergent solution in comparison with domestic dishwashing. A generally desirable reduction in the energy requirement and in the requirement for detergent solution or generally for surfactants or other chemical additives must however not be carried out at the expense of a cleaning result and in particular the hygiene effect achieved. Therefore, various hygiene standards for commercial washing are provided, such as DIN 10510 in Germany or the so-called NSF3 standard in the USA for example. The latter stipulates, for example, that specific temperatures and concentrations of disinfectants have to be maintained in the final rinse operation and that a warning has to be output in the event of deviations.

EP 2 053 959 B1 describes a method for assessing and ensuring the thermal hygiene effect in a multi-tank washer. The temperature within at least one treatment zone is transmitted to a machine controller by means of at least one temperature sensor. On the basis of the temperature, a heat input onto the washware is ascertained and this heat input is compared with a prespecified heat input. The transportation speed is varied in order to control the actual heat input.

DE 10 2006 014 464 B3 discloses a device for cleaning dishes, which device has a transportation device for the items to be cleaned. Said transportation device can transport the items to be cleaned through at least one cleaning chamber at different transportation speeds. Furthermore, a metering device for detergent is provided, which metering device dispenses a specific quantity of detergent into the cleaning chamber. The metering device selects the quantity of detergent to be dispensed depending on the transportation speed.

DE 10 2006 019 546 A1 describes a metering device for a batch washer with a dispensing unit and a controller for the quantity of detergent which is to be dispensed, which controller actuates the dispensing unit. The metering device has a control unit which interrupts and/or chokes or intensifies actuation of the dispensing unit by the controller for specific time intervals.

EP 1 886 615 B1 describes a dishwasher which is designed such that dinnerware is washed with wash water. The wash water is contained in a wash water tank and is collected in the wash water tank after the washing operation. A portion of the wash water which is contained in the wash water tank is replaced by supplied water after each wash cycle. The dishwasher furthermore has a detergent supply device which supplies a detergent to the wash water and which increases a supplied quantity of the detergent on the basis of the number of wash cycles.

DE 10 2013 203 933 A1 discloses a method for cleaning items to be cleaned, in which method at least one rinse liquid is applied to the items to be cleaned. In this case, supply of at least one component of the rinse liquid is increased from a starting value to an equilibrium value as the cleaning duration increases.

DE 10 2014 102 970 A1 describes a conveyor washer for washing washware. At least one final rinse zone with at least one final rinse nozzle for spraying final rinse liquid onto the washware and one metering device, which is associated with the final rinse zone, for adding a disinfectant to the final rinse liquid in a metered manner are provided in said conveyor washer. Furthermore, a sensor device is provided, which sensor device is designed to detect the concentration of disinfectant in the final rinse liquid which is sprayed in the final rinse zone. A control device is further provided, which control device is designed to compare the value for the concentration of disinfectant, which value is detected by the sensor device, with predefinable concentration values and, in the case of excessively high deviations in the concentration of disinfectant from the predefinable concentration values, to interrupt the washing process or to output a warning signal to an operator.

DE 10 2009 024 569 A1 describes a method for operating a conveyor washer. The conveyor washer has at least one pre-rinse zone with a pre-rinse nozzle for spraying pre-rinse liquid onto the washware and at least one final rinse zone with at least one final rinse nozzle for spraying final rinse liquid onto the washware. At least a portion of the sprayed final rinse liquid is reused as pre-rinse liquid. A metering device which is associated with the final rinse zone is provided for adding a disinfectant to the final rinse liquid in a metered manner. Furthermore, a metering device which is associated with the pre-rinse zone is additionally provided for adding a disinfectant to the pre-rinse liquid in a metered manner. A sensor device is further provided, which sensor device is designed for detecting the concentration of disinfectant in the pre-rinse liquid which is sprayed in the pre-rinse zone. A control device is further provided, which control device is designed to actuate one of the metering devices in such a way that disinfectant is added in a metered manner depending on the concentration of disinfectant which is detected by the sensor device.

DE 10 2011 007 507 A1 describes a conveyor washer with at least one wash zone and at least one final rinse zone and also with a transportation device for transporting washware through the at least one wash zone and the at least one final rinse zone. In order to reduce the consumption of disinfection chemicals and energy but to nevertheless maintain an optimum final rinse result, it is proposed according to this document that the final rinse liquid which is sprayed in the final rinse zone contains disinfection chemicals which are added in a metered manner, and that at least one additional final rinse zone which is connected downstream of the final rinse zone is provided for spraying fresh water without disinfection chemicals onto the washware to be treated. The at least one additional final rinse zone has an associated collecting device for collecting liquid which is sprayed in the additional final rinse zone. A liquid transfer system is further provided, by means of which liquid transfer system the liquid collected in the collecting device can be supplied directly to the wash zone.

DE 10 2012 213 271 A1 describes a washer which is embodied in the form of a conveyor washer or in the form of a batch washer and has at least one wash system for spraying wash liquid in a wash zone or during a washing phase and at least one final rinse system for spraying final rinse liquid in a final rinse zone or during a final rinse phase, wherein a control device is further provided for actuating the at least one wash system and/or the at least one final rinse system in accordance with a predefined sequence program. In order to be able to save resources during operation of the washer, wherein the requirements in respect of the hygienic operation of the washer defined in the respectively locally applicable hygiene guidelines (hygiene guidelines applicable within territorial limits) are simultaneously met, it is provided according to this document that at least one first sequence program is stored in the control device, which first sequence program has been created taking into account requirements in respect of hygienic operation of a commercial washer which are applicable in a first territorial region, and that at least one second sequence program is stored in the control device, which second sequence program has been created taking into account requirements in respect of hygienic operation of a commercial washer which are applicable in a second territorial region.

DE 10 2008 024 543 A1 describes a method for operating a washer. In this case, a wash pump is actuated during a wash process in such a way that a wash liquid of at least one wash nozzle is at least temporarily supplied via the line system. Furthermore, a profile of a hydrostatic pressure of the wash liquid in a line system is recorded and compared with a prespecified pressure profile. If the recorded pressure profile differs from the prespecified pressure profile, an automatic control action is taken in the washing process, a fault message is output by means of an optical and/or acoustic interface of the washer or a message is output to a remote servicing point by means of a remote control interface of the washer, depending on the size and the time gradient of a difference between the prespecified pressure profile and the recorded pressure profile.

WO 2011/062790 A2 discloses a washing device in which a sensor and a control device for detecting a volumetric flow rate of a liquid in a pipe system and for comparing a profile of said volumetric flow rate with a profile of a prespecified flow rate are provided. The control device is designed to intervene with automatic control or to output a warning in the event of a deviation.

These known methods and cleaning devices with thermal/chemical methods describe measuring and varying the temperature in order to achieve a desired hygiene effect and to maintain hygiene standards. Methods and cleaning devices of this kind do not allow accurate control and monitoring of the hygiene effect. In addition, adequate hygiene reliability can be achieved only with the use of a large amount of the resources energy and chemical additives, and this leads to a high level of expenditure for the operator and is disadvantageous for the environment.

SUMMARY

This disclosure teaches a method and a cleaning device which at least largely avoid the disadvantages of known methods and cleaning devices and improves hygiene reliability while using a low level of resources.

In the text which follows, the terms "have," "encompass," "comprise" or "include" or any grammatical departures therefrom are used non-exclusively. Accordingly, these terms can refer either to situations in which, besides the features introduced by these terms, no further features are present, or to situations in which one or more further features are present. For example, the expression "A has B," "A encompasses B," "A comprises B" or "A includes B" can refer either to the situation in which, apart from B, no further element is present in A (i.e., to a situation in which A exclusively consists of B), or to the situation in which, in addition to B, one or more further elements are present in A, for example element C, elements C and D or even further elements.

Furthermore, it should be noted that the terms "at least one" and "one or more" and grammatical modifications of these terms, if they are used in association with one or more elements or features and are intended to express the fact that the element or feature can be provided singularly or multiply, generally are used only once, for example when the feature or element is introduced for the first time. When the feature or element is subsequently mentioned again, the corresponding term "at least one" or "one or more" is generally no longer used, without restricting the possibility that the feature or element can be provided singularly or multiply. In the same connection, it shall be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "cleaning chamber," "influencing variable" and "hygiene value share," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Furthermore, in the text which follows, the terms "preferably," "in particular," "for example" or similar terms are used in conjunction with optional features, without alternative embodiments being restricted thereby. In this regard, features which are introduced by these terms are optional features, and the scope of protection of the claims, and in particular of the independent claims, is not intended to be restricted by these features. In this regard, the invention, as will be recognized by the person skilled in the art, can also be carried out using other configurations. In a similar way, features which are introduced by "in one embodiment of the invention" or by "in one exemplary embodiment of the invention" are understood as optional features, without alternative configurations or the scope of protection of the independent claims being intended to be restricted thereby. Furthermore, all possibilities of combining the features introduced by these introductory expressions with other features, be they optional or non-optional features, are intended to remain unaffected by these introductory expressions.

A first aspect of this disclosure proposes a method for cleaning items to be cleaned. Here, items to be cleaned can be understood to mean, in general, any items which can be subjected to cleaning or a cleaning method. Without restricting other possible refinements, reference is made below to items to be cleaned in the form of washware. Here, washware is intended to comprise any objects which are used to prepare, serve or store food and drinks. Examples which can be mentioned here include crockery such as cups, plates, glasses, dishes or bowls. Furthermore, pots, trays, cutlery, warming devices or similar devices can be mentioned. However, it should be expressly noted that other types of items to be cleaned can also be cleaned, such as industrial piece goods, bulk goods, containers or other types of items to be cleaned for example.

Cleaning can be understood to mean both removing adhering soiling or other impurities from the items to be cleaned and also a germ-reducing and/or germ-killing effect or even disinfecting effect. Hygienization is understood to mean, in principle, both removal of germs, in particular a germ-reducing and/or germ-killing or even disinfecting effect, and also removal of substances such as chemicals, for example residues of additives of the at least one cleaning fluid.

A cleaning device having at least one cleaning chamber and at least one application device (also referred to herein as "applicator") for applying at least one cleaning fluid to the items to be cleaned in the cleaning chamber is used in the method. Within the scope of this disclosure, a cleaning device is intended to be understood to mean, in general, a device which is configured to at least partially remove adhering impurities and/or germs from items to be cleaned. The cleaning device can be, for example, a dishwasher, in particular a commercial dishwasher, for example an automatic programmed dishwasher and/or a pass-through dishwasher. However, as an alternative or in addition, the cleaning device can also be entirely or partially configured as a cleaning and disinfection appliance, for example as a cleaning device which is configured to clean containers for receiving human excreta. In general, reference can be made in this respect to the cleaning devices described in DE 10 2004 056 052 A1 and/or in DE 10 2007 025 263 A1. The cleaning device can also be a washer as can be used for cleaning containers in the field of food production and/or food-processing. Furthermore, the cleaning device may be a disinfection washer, for example a washer for cleaning and disinfecting breathing masks. However, other refinements are also conceivable in principle.

The cleaning device can be configured, in particular, as a conveyor washer, in particular as a pass-through dishwasher. Here, a conveyor dishwasher is intended to be understood to mean a dishwasher, that is to say a machine for cleaning washware in the form of dishes which is configured to transport the washware through a cleaning chamber. In particular, said conveyor dishwasher may be a flight-type dishwasher and/or a rack conveyor dishwasher, that is to say a dishwasher in which the crockery is transported through the cleaning device by means of a conveyor belt, for example a conveyor belt on which the crockery is placed directly and/or on which one or more racks carrying the crockery to be cleaned are placed. The conveyor dishwasher can be configured, in particular, for commercial use, for example in one or more of the abovementioned facilities for mass catering. However, other types of cleaning devices are also possible in principle.

The cleaning fluid can be, for example, a cleaning liquid and/or a gaseous cleaning fluid. For example, this cleaning fluid can comprise a cleaning liquid, for example an aqueous cleaning liquid, for example water in the form of fresh water and/or with one or more additives, for example with one or more detergent concentrates and/or one or more final rinse aid concentrates and/or one or more disinfectants. For example, the cleaning fluid can have one additive or a plurality of additives, for example at least one additive selected from the group consisting of a detergent concentrate, a final rinse aid and a disinfectant. As an alternative or in addition, the cleaning fluid can comprise, for example, steam. However, other refinements are also conceivable in principle. The at least one cleaning fluid can comprise, in principle, at least one cleaning liquid for example, in particular at least one aqueous cleaning liquid. Other types of cleaning fluids can also be used in principle. A cleaning fluid can therefore be understood to mean any desired fluid, in particular a liquid, which can have a cleaning effect on the items to be cleaned.

Here, a cleaning chamber is understood to mean, in general, a chamber in which the above-described cleaning process for the items to be cleaned is completely or partially carried out. In particular, the cleaning fluid or one of several cleaning fluids is/are applied in a cleaning chamber. Furthermore, the cleaning device can comprise at least one transportation device (also referred to herein as a "transporter") which is configured to transport the items to be cleaned in a transportation direction from an inlet region, through the cleaning chamber, to an outlet region. The chamber is preferably completely or partially enclosed by a housing. In particular, the cleaning chamber can be of tunnel-like design or comprise a portion of a tunnel, for example with an inlet and an outlet, wherein the items to be cleaned are inserted into the cleaning chamber at the inlet and exit from the cleaning chamber at the outlet. An inlet is therefore intended to be understood to mean a region outside the cleaning chamber which is arranged directly in front of the cleaning chamber in the transportation direction and in which the items to be cleaned can be placed on the transportation device. Accordingly, an outlet is intended to be understood to mean a region outside the cleaning chamber which is arranged directly behind the cleaning chamber in the transportation direction and in which the items to be cleaned can be removed from the transportation device. Within the scope of this disclosure, a transportation device or transporter is intended to be understood to mean, in general, any desired device which is configured to transport the items to be cleaned through the cleaning chamber in the transportation direction. For example, this transportation device can be selected from amongst a belt conveyor device with at least one conveyor belt, a latch transportation system and a roller transportation device having at least one transportation roller or a plurality of transportation rollers, for example one or more driven transportation rollers by means of which, for example, the items to be cleaned can be transported directly and/or one or more racks which hold the items to be cleaned can be transported through the cleaning chamber in the transportation direction. The transportation device can have, for example, at least one drive, for example at least one drive motor. For example, said drive can be a drive which drives at least one conveyor belt and/or at least one transportation roller or another type of transportation element of the transportation device.

Here, an application device or applicator is intended to be understood to mean, in principle, any desired device or combination of devices by means of which the cleaning fluid can be applied to the items to be cleaned, for example by spraying, irradiating or dripping the cleaning fluid onto the items to be cleaned. For example, the application device can have at least one nozzle system. Therefore, for example, one or more nozzle systems can be provided in the conveyor dishwasher. If a plurality of cleaning zones are provided for example, each cleaning zone can have for example at least one associated nozzle system of this kind. For example, the cleaning device can be configured in such a way that the items to be cleaned pass the cleaning zones one after the other. For example, reference can be made to the above-mentioned prior art for an arrangement of cleaning zones of this kind.

The method comprises the following steps:
a. prespecifying a desired hygiene value which is to be achieved with the cleaning;
b. time-resolved recording of at least two influencing variables which have an influence on a hygienization of the items to be cleaned;
c. determining hygiene value shares from the influencing variables using a prespecified relationship between each influencing variable and the respective hygiene value share of said influencing variable;
d. ascertaining an expected actual hygiene value at the end of the cleaning from the hygiene value shares;
e. comparing the expected actual hygiene value with the desired hygiene value; and
f. influencing at least one influencing variable depending on the result of the comparison.

The method steps can be carried out in said order or else in another order. Furthermore, one or more of said method steps can also be carried out in parallel with respect to time, with an overlap with respect to time or else at the same time. Furthermore, one or more of the method steps can be repeatedly or permanently carried out individually or in groups.

A hygiene value is intended to be understood to mean, in general, a variable which quantifies a hygiene result. For example, the hygiene value can be a hygiene level. For example, the hygiene value can be selected from A0 values or H.U.E. values; a measure of a reduction in a population of a target germ. A0 values and H.U.E. values are a measure of the reduction, or mortality rate, of a target germ due to a thermal action. The higher the acting temperature, the greater the germ-reducing effect per unit time. For example, more A0 values and H.U.E. values per second can be reached at a relatively high temperature. However, operation of the cleaning device at low temperatures may be desirable, for example for reducing use of resources such as energy for heating. The reduction in the target germ can be influenced by further variables, such as the influencing variables, mechanics and chemistry for example, in particular by a concentration or composition of at least one additive of the cleaning fluid. An SUE value (sanitation unit equivalent) per second can be a measure of the reduction in the target germ, which measure takes into account a dependency on the temperature and the detergent chemicals used, where $$SUE/sec = Ae^{BT},$$

where $A=1/7000000$ and $B=0.191$. Here, a SUE value of 100 corresponds to a 5 log-level reduction in the target germ. The parameters A and B are empirical values determined using a population of *Staphylococcus aureus* as target germ population. The method is not linked to said target germ population. For example, the method can be matched to altered requirements and other germs can be imagined as target germ, for example *Enterococcus faecium*. The SUE method can allow the concentration or composition of the at least one additive of the cleaning fluid on the hygiene effect to be taken into account and thereby allow operation of the cleaning device at low temperatures with the hygiene effect remaining the same. The hygiene value can preferably be a SUE value.

Furthermore, in terms of the hygiene value, a distinction can be drawn between a desired hygiene value and an actual hygiene value. A desired hygiene value is intended to be understood to mean a hygiene result which the cleaning device is intended to achieve with the cleaning, in particular at the end of the cleaning process, for example an end of a cleaning program in a single-chamber washer and/or an automatic programmed washer and/or, for example, at an end of a tunnel in the case of a conveyor dishwasher. An actual hygiene value is intended to be understood to mean a hygiene result which the cleaning device actually achieves.

The desired hygiene value can be selected from the group consisting of: an A0 value which is to be achieved overall with the cleaning according to DIN EN ISO 15883; a hygiene level which is to be achieved according to DIN 10510, at the desired prespecifications for tank and boiler temperatures according to DIN 10510; a number of HUE units according to the NSF3 standard which are to be achieved overall with the cleaning; a reduction in a population of a target germ which is to be achieved overall with the cleaning, in particular a reduction in the population of *Staphylococcus aureus* which is to be achieved overall with the cleaning. The desired hygiene value can correspond to 99.999% death of a population of *Staphylococcus aureus*. In particular, the desired hygiene value can be a SUE value. Prespecification of a desired hygiene value which is to be achieved with the cleaning can be understood to mean providing a desired hygiene value. For example, the prespecification can comprise selecting a desired hygiene value, for example from a list, and/or entering a desired hygiene value, for example into a man/machine interface of the cleaning device, in particular a controller of the cleaning device.

Within the scope of this disclosure, an influencing variable is intended to be understood to mean, in general, a quantifiable variable which can influence the operation of the cleaning device and/or a cleaning result of the cleaning device in some way. The hygienization, also called the hygiene effect, for cleaning sequences can be determined by various influencing variables. The influencing variables can be selected from the group consisting of: a duration of the cleaning; at least one temperature of the at least one cleaning fluid; at least one measurement variable which is characteristic of a mechanical action of the at least one cleaning fluid on the items to be cleaned, in particular a pressure and/or a flow rate of the at least one cleaning fluid; at least one concentration of at least one disinfectant in the at least one cleaning fluid; at least one concentration of at least one detergent concentrate in the at least one cleaning fluid; at least one pH value of the at least one cleaning fluid; at least one measurement variable which is characteristic of an effect of a final rinse operation. The influencing variables can influence each other. The hygiene effect can be presented as a pie chart in which the influencing variables represent segments of a circle which have to add up to form the entire circle. A reduction in one of these influencing variables can respectively be compensated for by increasing one or more of the other influencing variables.

The at least two influencing variables can comprise, as first influencing variable, at least one temperature of the at least one cleaning fluid and furthermore at least one further influencing variable. Recording an influencing variable is understood to mean, in general, determining and/or detecting and/or measuring the influencing variable, in particular a measurement value, and/or a measure of the influencing variable. Time-resolved recording of the influencing variable is understood to mean, in general, recording of the influencing variable over time and/or development of the influencing variable over time. The time-resolved recording of the at least two influencing variables can take place at prespecified or prespecifiable times or at prespecified or prespecifiable intervals. In particular, the time-resolved recording can take place before influencing the influencing variable.

For example, the cleaning device can have at least one sensor for recording the influencing variables. Within the scope of this disclosure, a sensor is intended to be understood to mean, in general, a device which is configured to record one or more measurement values of the influencing variables, preferably in the form of one or more of electronic measurement values. The measurement values can be of analog and/or digital form. The sensor can comprise, for example, at least one sensor element which is configured to generate at least one sensor signal, for example an analog or digital sensor signal, in accordance with the state variables which are to be recorded. However, in addition to the at least one sensor element, the sensor can comprise one or more further elements. For example, the sensor can comprise, in particular, one or more supply lines which are connected to the sensor element and/or other elements of the sensor. Furthermore, for example, at least one actuating and/or evaluating circuit can be provided, which actuating and/or evaluating circuit can be connected to the sensor element and is often also referred to as measurement printed circuit board or simply only as printed circuit board. Furthermore, the sensor can comprise further elements, such as at least one analog/digital converter (A/D converter) and/or at least one signal line and/or data line and/or an interface for example. The overall assembly, which is made up of the at least one sensor element and optionally the at least one further element of the sensor, can together form a sensor system and/or a measurement chain of the sensor, which measurement chain can ultimately be connected to a controller. The sensor itself can therefore be a sensor system or can be a constituent part of a sensor system. The measurement chain and the design of said measurement chain can ultimately determine how a determined value of the influencing variables and/or a change in this value act on one or more sensor signals which are made available to the controller. Therefore, overall, the sensor can comprise at least one sensor element and at least one further element, in particular at least one further element selected from the group comprising: an actuating and/or evaluating circuit (in particular for processing at least one measurement value or sensor value), an interface, an analog/digital converter (A/D converter), a wireless and/or wired transmission element, a signal line and/or data line, a voltage supply, an A/D converter, a display element, a data memory, a radio module. However, other refinements are also possible.

The basis for carrying out the present method can be corresponding control hardware and/or control software of the cleaning device, which control hardware and/or control software can be entirely or partially implemented in the controller or else can be at least partially integrated into other constituent parts of the cleaning device.

For example, the sensor can comprise at least one temperature sensor, in particular at least one sensor element in the form of, for example, a temperature-dependent resistor, for example an NTC and/or a PTC.

The cleaning device can be configured to determine a current value of a metering operation of a disinfectant in the at least one cleaning fluid and/or at least one concentration of the at least one detergent concentrate in the at least one cleaning fluid and/or at least one pH value. For example, the cleaning device can be configured to determine a detergent concentration in a washing liquid. For example, the cleaning device can be configured to determine a composition of the detergent, in particular a pH value of the washing liquid in the recirculation tank. The cleaning device can have at least one sensor selected from the group consisting of a conductivity electrode, a pH probe, a redox probe, a chlorine sensor. Recording can take place, for example, in a wash tank of the cleaning device. In particular, recording can take place in a wash tank of the cleaning device in which corruption of the measurement values by incorporation of particles of dirt, for example table salt, is low, for example in a last wash tank. Recording a concentration of a detergent concentrate can take place using a quantity of detergent, which is supplied to a cleaning zone, and a quantity of regeneration water. The cleaning device can have at least one throughflow sensor, and/or the quantity of detergent can be determined by means of scales. The quantity of regeneration water can be determined, for example, from a run time of a liquid transfer device.

The cleaning device can have at least one sensor for recording at least one variable which characterizes a mechanical action of the at least one cleaning fluid on the items to be cleaned, in particular a pressure and/or a flow rate of the at least one cleaning fluid. For example, the sensor can comprise at least one sensor element in the form of a pressure sensor, for example in the form of a micromechanical pressure sensor. The pressure sensor can be configured to record a system pressure in a washing system of the cleaning device. For example, the sensor can have a baffle plate sensor which can record an effect of individual nozzles, so-called reference nozzles. However, other refinements are also conceivable.

A hygiene value share is intended to be understood to mean, in general, a hygiene value per time period. The hygiene value share can be a value which is to be achieved (desired value). The hygiene value share can be a value which is actually achieved (actual value). A time period can be understood to mean, in particular, a time duration and/or a unit of time. An actual hygiene value which is achieved in a period of time can be determined by adding up the hygiene value shares in the period of time. For example, the hygiene value shares can be added up over the length of a treatment zone or the time duration for which the items to be cleaned are in this zone and therefore a hygiene value share for the treatment zone can be determined. The hygiene value share for the treatment zone can be referred to as the hygiene value share which this zone contributes to the total result. As an alternative or in addition, a hygiene value share for a fixed time period can be taken into account, for example a hygiene value share per second. The hygiene value share can comprise a hygienization rate. A hygienization rate is intended to be understood to mean a change over time. The relationship between the influencing variables and the respective hygiene value shares of said influencing variables can be prespecified by at least one of the following prespecifications: at least one calibration curve, in particular at least one curve relating to a hygiene effect, wherein the calibration curve respectively indicates a relationship between the respective hygiene value share of the influencing variable and a further influencing variable, wherein the at least one further influencing variable is kept constant; at least one family of curves comprising a plurality of calibration curves, wherein the calibration curves each indicate a relationship between the respective hygiene value share of the influencing variable and a further influencing variable, wherein the at least one further influencing variable is kept constant within each calibration curve of the family of curves, wherein the at least one further influencing variable distinguishes between the calibration curves of the family of curves; at least one calibration table, wherein the calibration table respectively indicates a relationship between the respective hygiene value share of the influencing variable and a further influencing variable, wherein the at least one further influencing variable is kept constant; at least one family of calibration tables comprising a large number of calibration tables, wherein the calibration tables each indicate a relationship between the respective hygiene value share of the influencing variable and a further influencing variable, wherein the at least one further influencing variable is kept constant within each calibration table of the family of tables, wherein the at least one further influencing variable distinguishes between the calibration tables of the family of tables. In this way, a dependency of the individual influencing variables in relation to one another can be determined. When taking into account at least two influencing variables, in particular all influencing variables, a multidimensional field can be determined, in which multidimensional field, as described in detail further below, the cleaning device, in particular the controller of the cleaning device, can vary the individual influencing variables.

The method can comprise at least one calibration. The relationship between each influencing variable and the respective hygiene value share of said influencing variable can be determined during the calibration. For example, the calibration can take place once, for example when first starting up the cleaning device. For example, the calibration can take place repeatedly, for example at prespecifiable or selectable time intervals. The relationship can be stored in at least one data memory, for example of the controller, after the calibration. For example, the relationship can be stored in a table, wherein, for example, the calibration curves are stored as discrete values. During the calibration, it is possible to determine how long is required, under respective constant conditions, including prespecified constant values of the influencing variables, until the prespecified desired hygiene value is achieved, in particular a prespecified reduction factor or a prespecified reduction in at least one target germ, wherein the hygiene value share is determined from this information about the time duration, taking into account an initial hygiene value, the desired hygiene value and the time duration.

An expected actual hygiene value is understood to mean, in general, an expected hygiene result which is achieved at the end of the cleaning. Ascertaining the expected actual hygiene value can comprise taking into account and/or adding up all previously achieved hygiene value shares, that is to say hygiene value shares achieved up to the time at which the expected actual hygiene value is ascertained. In particular, all hygiene value shares acting on the items to be cleaned since a start time of a cleaning program can be taken into account and/or added up. The expected actual hygiene value can be a prediction of the actual hygiene value at the end of the cleaning. The expected actual hygiene value at the end of the cleaning can be determined from the hygiene value shares assuming that the current influencing variables remain unchanged for the rest of the cleaning. The expected actual hygiene value at the end of the cleaning can be calculated from the hygiene value shares using at least one algorithm selected from the group consisting of: integration of the sum of the hygiene value shares of the influencing variables over the expected remaining duration of the cleaning; a totality of the Riemann sums with respect to time of the respective hygiene value shares of the influencing variables over the expected remaining duration of the cleaning. An end of cleaning can be understood to mean an end in respect of time in a single-chamber machine and/or automatic programmed washer and/or an end of a tunnel in the case of a conveyor washer.

The method comprises comparing the expected actual hygiene value with the desired hygiene value. Comparison of the expected actual hygiene value with the desired hygiene value is understood to mean, in general, determining an equality or a deviation in, in particular an overshooting and/or undershooting of, the expected actual hygiene value and the desired hygiene value. The comparison can comprise a mathematical comparison. In particular, method step e. can comprise identifying whether the expected actual hygiene value is lower than the desired hygiene value.

The method comprises influencing at least one influencing variable depending on the result of the comparison. In particular, the cleaning device can be configured to influence at least one influencing variable in such a way that an actual hygiene value which is actually achieved at the end of the cleaning corresponds to the desired hygiene value.

Influencing is generally understood to mean a change and/or variation and/or adjustment and/or regulation of at least one influencing variable. Influencing of the at least one influencing variable can take place at prespecified or prespecifiable times. For example, an influencing time can be stored in a data memory of the controller of the cleaning device. The controller can be configured to prespecify an influencing time. For example, an influencing time can be selected, in particular by the controller and/or a user. Influencing can take place at a time during a cleaning program. For example, comparing the expected actual hygiene value and the desired hygiene value can take place at the end of a cleaning step of the cleaning program and influencing of the at least one influencing variable can take place in a subsequent cleaning step. For example, in a conveyor washer, influencing can take place at a prespecified time during the transportation of the items to be cleaned, for example at a specific location, in particular between two cleaning zones. As mentioned above, a relationship between the respective hygiene value share of the influencing variable and a further influencing variable, for example in the form of a family of curves, can be determined, for example in a calibration step. The cleaning device, in particular the controller, can be configured to determine a dependency of the individual influencing variables, in particular at least two influencing variables, in relation to one another. The cleaning device, in particular the controller, is preferably configured to determine a dependency of each individual influencing variable in relation to each other influencing variable. The cleaning device can be configured to determine a multidimensional field in which the individual influencing variables can be varied. Influencing can take place only within prespecified and/or prespecifiable limits for each influencing variable.

For example, the duration of the cleaning can be changed when it is identified during the comparison that the expected actual hygiene value differs from the desired hygiene value. In particular, the duration of the cleaning can be increased when it is identified that the expected actual hygiene value is lower than the desired hygiene value. In particular, the duration of the cleaning can be reduced when it is identified that the expected actual hygiene value is higher than the desired hygiene value. It is possible for at least one measure for changing the duration of the cleaning to be used, said measure being selected from the group consisting of: at least one program duration of at least one cleaning program is changed; at least one transportation speed of at least one transportation device, by means of which the items to be cleaned are transported through the at least one cleaning chamber, is changed. For example, a program run time can be increased or shortened. For example, an action duration can be increased or shortened. A change in a transportation speed of a transportation device, for example a conveyor belt, can take place for example in the case of a conveyor washer. For example, the transportation speed can be increased or slowed down. The transportation speed can be reduced down to intermittent operation, in the case of which the transportation device is stopped. In the case of intermittent operation, regions of the transportation device, in particular of the conveyor belt, can remain in a cleaning zone, for example the fresh water rinse arrangement, so that the action time is extended. For example, in the case of cleaning devices with thermal disinfection, the transportation device can be stopped when a specific temperature is undershot. For example, in the case of cleaning devices with chemical disinfection, the transportation device can be stopped when the disinfection component is missing. The transportation speed can additionally be reduced when the time-resolved recording of the at least one influencing variable has not taken place and/or a sensor signal has not been generated by the at least one sensor for recording the influencing variable and/or transmitted to the controller and/or the controller, in particular the data memory, does not contain any information and/or a value of the influencing variable.

For example, at least one concentration of at least one additive in the at least one cleaning fluid can be changed when it is identified that the expected actual hygiene value differs from the desired hygiene value. The at least one concentration of the at least one additive in the at least one cleaning fluid can be increased when it is identified that the expected actual hygiene value undershoots the desired hygiene value. Therefore, it is possible, for example, to compensate for a relatively low hygiene effect from the thermal influence, for example in the case of a drop in a temperature of the cleaning fluid, for example a washing liquid in a recirculation tank, by increasing the concentration of the at least one additive in the at least one cleaning fluid and/or, as described further below, changing the composition of at least one additive in the at least one cleaning fluid, without extending a run time, in particular a washing time. The additive can comprise at least one substance selected from the group consisting of a detergent concentrate and a disinfectant, in particular chlorine. Other disinfectants can be or contain, for example, bromine, iodine or hydrogen peroxide. Within the scope of the present application, the expression 'detergent' is used synonymously with the expression 'additive.'

For example, an increase in a share and/or additional metering of disinfection components can take place. For example, the controller can be configured to activate at least one metering device of the cleaning device more frequently and/or for a longer time duration. For example, the controller can be configured to increase a delivery volume of the metering device in the event of continuous running of the metering device. In one embodiment, the cleaning device can have a first and a second metering device. The first metering device can be operated continuously, for example at a basic setting. The controller can be configured to activate the second metering device and therefore supply additional additives in the case of the concentration and/or the metering being influenced. This is particularly advantageous since the first and the second metering device can be of simple design. The additives supplied by the first and the second metering device can differ. For example, an additive of the second metering device can contain a disinfection component. Therefore, cleaning at low temperatures can be rendered possible in particular. For example, a user can select a low temperature and/or the cleaning device can be configured to identify that washing can be performed at low temperatures and to reduce temperatures in the cleaning process.

The method can comprise a detection step in which, in particular before a change in a concentration and/or metering, determining a current concentration and/or metering takes place. For example, at least one, above-described, sensor can be used in the detection step, which sensor is configured to determine the current value for metering of a disinfectant in the at least one cleaning fluid and/or at least one concentration of the at least one detergent concentrate in the at least one cleaning fluid and/or at least one pH value. The change in the concentration and/or metering can take place within a prespecifiable and/or prespecified limit. For example, an upper limit for metering can be 4 g of detergent per liter of tank contents.

For example, at least one mechanical application of the at least one cleaning fluid to the items to be cleaned can be changed when it is identified during the comparison that the expected actual hygiene value differs from the desired hygiene value. In particular, an intensity of the mechanical application can be increased when it is identified that the expected actual hygiene value is lower than the desired hygiene value. In particular, an intensity of the mechanical application can be lowered when it is identified that the expected actual hygiene value is higher than the desired hygiene value. For example, at least one measure for changing the intensity of the mechanical application can be used, which measure is selected from the group consisting of: at least one pressure of the at least one cleaning fluid is changed; at least one flow rate of the at least one cleaning fluid is changed. For example, increasing the mechanical effect can take place by switching on further application devices, for example further nozzles. For example, a pumping capacity of the cleaning device can be increased, for example by using a series circuit of pumps or at least one frequency converter.

The method can comprise a detection step in which, in particular before a change in a mechanical effect, determining of a current mechanical effect takes place. As stated above, the cleaning device can have sensors which are configured to monitor the mechanical effect of the washing system, in particular the application device. The sensors for monitoring the mechanical effect can be configured to identify malfunctions in the washing system. The sensors for monitoring the mechanical effect can be configured to identify that a system pressure is insufficient and/or that individual nozzles produce too small a jet of water or no jet of water. The sensors for monitoring the mechanical effect can be configured to transmit detection results of this kind to the controller. The controller can be configured to influence another influencing variable as the mechanical effect in order to equalize malfunctions in the washing system, in particular the application device, in order to achieve a desired hygiene value. A change in the mechanical effect can take place within a predefinable and/or predefined limit. For example, an upper limit for a mechanical effect can be provided in that damage to the items to be cleaned is intended to be avoided.

For example, a volume flow in the final rinse arrangement can be increased, for example a fresh water final rinse arrangement and/or pump final rinse arrangement. The method can comprise a detection step in which, in particular before a change in the volume flow of the final rinse arrangement, determining of a current volume flow takes place. For example, the cleaning device can have at least one sensor which is configured to determine a throughflow in the fresh water final rinse arrangement. For example, the cleaning device can have at least one sensor which is configured to record a pressure and/or throughflow in the pump final rinse arrangement.

For example, an increase in the temperature, in particular in individual tanks and/or cleaning zones, can take place. The method can comprise a detection step in which, in particular before a change in the temperature, determining of a current temperature takes place, for example using one or more temperature sensors.

In method step f., an influencing measure can be used for influencing the at least one influencing variable, wherein the influencing measure takes place depending on a prespecified and/or prespecifiable hierarchy of measures. The hierarchy of measures can be stored in the controller, for example in the form of a program code. The hierarchy of measures can be selected taking into account a decision basis selected from the group consisting of: speed at which a process can be influenced, for example inertia of sensors and of the process; real expenditure for influencing the at least one influencing variable, for example expenditure on equipment, costs and susceptibility to faults; costs to the user and/or operator, for example costs of cleaning chemicals. For example, the temperature of the at least one cleaning fluid can be increased when the desired hygiene value is undershot. The cleaning device can be configured to identify whether the required temperature is reached within a prespecified time window after the increase in temperature is triggered and to initiate regulation of the metering if said temperature is not reached. Influencing the metering can have a great influence on operating costs. In addition, tracking the concentration may require longer than influencing other influencing variables, so that changing the metering can be arranged after influencing of other influencing variables in the hierarchy of measurements, in particular at the end of the hierarchy of measurements. In particular a so-called overkill due to excessive detergent, in particular additives, can be avoided in this way and optimum use of the cleaning chemicals in an advantageous manner in respect of the environment and expense to the operator can be achieved. For example, influencing can take place in the following order:

influencing of the duration of the cleaning;
influencing of the mechanical effect;
influencing of the effect of a final rinse arrangement;
influencing of the concentration and/or metering and/or at least one pH value;
influencing of the temperature of the at least one cleaning fluid.

In the method, the items to be cleaned can be transported through the at least one cleaning chamber by means of the at least one transportation device.

The items to be cleaned can comprise a plurality of items to be cleaned, wherein each item is allocated a hygienization account in which previous hygienization units to which the item has been subjected are cumulatively stored. A hygienization unit is understood to mean a variable which quantifies the influence on germ reduction. A number of hygienization units can be assigned to each hygienization process depending on the influence on germ reduction. For example, a desired hygiene result for one item to be cleaned can be 1000 hygienization units, so that 1000 hygienization units are required to achieve the desired hygiene value. Zero hygienization units can mean that the item has not previously been subjected to any hygienization process. A hygienization account can be understood to mean, in principle, a stored number of accumulated hygienization units. The hygienization account can be stored, for example, in a data memory of the controller. The items to be cleaned can comprise a plurality of items to be cleaned, wherein the transportation device is subdivided into sections, wherein each section is allocated a hygienization account in which previous hygienization units to which the item held in the respective section has been subjected are cumulatively stored. The hygienization account can be reset to zero when a fault in the cleaning process is established. For example, the hygienization account can be set to zero when the cleaning chamber is opened.

The cleaning chamber can be subdivided into a plurality of cleaning zones, wherein each cleaning zone has at least one application device, wherein the items to be cleaned are transported through the cleaning zones by means of the transportation device one after the other. The method can comprise at least one checking step, wherein the checking step is carried out until the items to be cleaned are located within the last cleaning zone in a transportation direction of the transportation device. During the checking step, the expected actual hygiene value can be once again compared with the desired hygiene value and at least one safety measure can be taken when the desired hygiene value is undershot. The safety measure can comprise at least one measure selected from the group consisting of: the transportation device is stopped; the transportation device is slowed down; a pressure of the cleaning fluid in the application device of the last cleaning zone is increased; a flow rate of the cleaning fluid in the application device of the last cleaning zone is increased. The last cleaning zone can be a final rinse zone, in particular a fresh water final rinse zone.

A further aspect proposes a cleaning device for cleaning items to be cleaned. The cleaning device comprises at least one cleaning chamber and at least one application device for applying at least one cleaning fluid to the items to be cleaned in the cleaning chamber. The cleaning device further comprises:

I. at least one data memory for storing a prespecification for a desired hygiene value which is to be achieved with the cleaning;
II. at least two measuring devices for time-resolved recording of at least two influencing variables which have an influence on a hygienization of the items to be cleaned;
III. at least one determining device for determining hygiene value shares from the influencing variables using a prespecified relationship between each influencing variable and the respective hygiene value share of said influencing variable;
IV. at least one evaluating device for ascertaining an expected actual hygiene value at the end of the cleaning from the hygiene value shares;
V. at least one comparing device for comparing the expected actual hygiene value with the desired hygiene value; and
VI. at least one influencing device for influencing at least one influencing variable depending on the result of the comparison.

The cleaning device can be configured, in particular, to carry out a method according to one or more of the refinements presented above. Accordingly, reference can be made to the above description for possible refinements of the cleaning device.

The cleaning device can have a controller. The data memory, the determining device, the evaluating device, the comparing device and the influencing device can be constituent parts of the controller. The controller can comprise at least one data processing device, in particular at least one processor or data processor. The data processing device can be programmed to allocate in each case one hygiene value share to the influencing variables on the basis of the prespecified relationship and to determine the expected actual hygiene value at the end of the cleaning from the hygiene value shares. The data processing device can further be programmed to compare the expected actual hygiene value with the desired hygiene value. The data processing device can further be programmed to identify whether the expected actual hygiene value is lower than the desired hygiene value. The data processing device can further be programmed to influence the at least one influencing variable depending on the result of the comparison.

The data memory can comprise at least one memory selected from a volatile data memory and a nonvolatile data memory.

A measuring device (also referred to as a "recorder") is understood to mean, in general, a device which is configured to record at least one influencing variable in a time-resolved manner. The measuring devices can comprise at least two sensors selected from the group consisting of: at least one temperature sensor for recording at least one temperature of the at least one cleaning fluid; at least one mechanical or fluidic sensor for recording at least one measurement variable of a mechanical action of the at least one cleaning fluid on the items to be cleaned, in particular at least one pressure sensor for recording at least one pressure of the at least one cleaning fluid and/or at least one flow sensor for recording at least one flow of the at least one cleaning fluid; at least one concentration sensor for recording at least one concentration of at least one disinfectant in the at least one cleaning fluid; at least one concentration sensor for recording at least one concentration of at least one detergent concentrate in the at least one cleaning fluid; at least one pH sensor for recording at least one pH value of the at least one cleaning fluid. In particular, the measuring device can be configured to carry out method step b.

A determining device is understood to mean, in general, a device which is configured to determine hygiene value shares from the influencing variables using a prespecified relationship between each influencing variable and the respective hygiene value share of said influencing variable. In particular, the determining device can be configured to carry out method step c. An evaluating device is understood to mean, in principle, a device which is configured to ascertain an expected actual hygiene value at an end of the cleaning from the hygiene value shares. A comparing device is understood to mean, in principle, a device which is configured to compare the expected actual hygiene value with the desired hygiene value. An influencing device is understood to mean, in general, a device which is configured to influence at least one influencing variable depending on the result of the comparison. As stated above, the cleaning device can have a controller, wherein the determining device, the evaluating device, the comparing device and the influencing device are constituent parts of the controller. For example, the determining device, the evaluating device, the comparing device and the influencing device comprise processors, in particular microprocessors.

The cleaning device can be selected from the group consisting of a conveyor washer and an automatic programmed washer.

The proposed method and the proposed cleaning device have numerous advantages over known methods and cleaning devices. Therefore, precise control and monitoring of the hygiene effect is possible and improvement in the operational reliability taking into account the hygiene aspects is possible. In particular, a so-called overkill due to excessive detergent, in particular additives, can be avoided and therefore optimum use of the cleaning chemicals in an advantageous manner in respect of the environment and expense to the operator can be achieved. In the case of a drop in a temperature of the cleaning fluid in the recirculation tank, increasing the concentration of the detergent and/or changing the composition of the detergent in the recirculation tank can compensate for a relatively low hygiene effect from the thermal influence, without extending a washing time.

In summary, the following embodiments are particularly preferred within the scope of this disclosure:

Embodiment 1: a method for cleaning items to be cleaned, wherein a cleaning device having at least one cleaning chamber and at least one application device for applying at least one cleaning fluid to the items to be cleaned in the cleaning chamber is used, wherein the method comprises the following steps:
  a. prespecifying a desired hygiene value which is to be achieved with the cleaning;
  b. time-resolved recording of at least two influencing variables which have an influence on a hygienization of the items to be cleaned;
  c. determining hygiene value shares from the influencing variables using a prespecified relationship between each influencing variable and the respective hygiene value share of said influencing variable;
  d. ascertaining an expected actual hygiene value at the end of the cleaning from the hygiene value shares;
  e. comparing the expected actual hygiene value with the desired hygiene value; and
  f. influencing at least one influencing variable depending on the result of the comparison.

Embodiment 2: the method according to the preceding embodiment, wherein method step e. further comprises identifying whether the expected actual hygiene value is lower than the desired hygiene value.

Embodiment 3: the method according to either of the preceding embodiments, wherein the hygiene value share comprises a hygienization rate.

Embodiment 4: the method according to one of the preceding embodiments, wherein the desired hygiene value is selected from the group consisting of: an A0 value according to DIN EN ISO 15883 which is to be achieved overall with the cleaning; a hygiene level which is to be achieved according to DIN 10510, at the desired prespecifications for tank and boiler temperatures according to DIN 10510; a number of HUE units according to the NSF3 standard which are to be achieved overall with the cleaning; a reduction in a population of a target germ which is to be achieved overall with the cleaning, in particular a reduction in the population of *Staphylococcus aureus* which is to be achieved overall with the cleaning.

Embodiment 5: the method according to the preceding embodiment, wherein the desired hygiene value corresponds to 99.999% death of a population of *Staphylococcus aureus*.

Embodiment 6: the method according to one of the preceding embodiments, wherein the influencing variables are selected from the group consisting of: a duration of the cleaning; at least one temperature of the at least one cleaning fluid; at least one measurement variable which is characteristic of a mechanical action of the at least one cleaning fluid on the items to be cleaned, in particular a pressure and/or a flow rate of the at least one cleaning fluid; at least one concentration of at least one disinfectant in the at least one cleaning fluid; at least one concentration of at least one detergent concentrate in the at least one cleaning fluid; at least one pH value of the at least one cleaning fluid; at least one measurement variable which is characteristic of an effect of a final rinse operation.

Embodiment 7: the method according to one of the preceding embodiments, wherein the at least two influencing variables comprise, as first influencing variable, at least one temperature of the at least one cleaning fluid and furthermore at least one further influencing variable.

Embodiment 8: the method according to one of the preceding embodiments, wherein the time-resolved recording of the at least two influencing variables takes place at prespecified or prespecifiable times or at prespecified or prespecifiable intervals.

Embodiment 9: the method according to one of the preceding embodiments, wherein influencing of the at least one influencing variable takes place at prespecified or prespecifiable times.

Embodiment 10: the method according to one of the preceding embodiments, wherein the relationship between the influencing variables and the respective hygiene value shares of said influencing variables is prespecified by at least one of the following prespecifications: at least one calibration curve, in particular at least one curve relating to a hygiene effect, wherein the calibration curve respectively indicates a relationship between the respective hygiene value share of the influencing variable and a further influencing variable, wherein the at least one further influencing variable is kept constant; at least one family of curves comprising a plurality of calibration curves, wherein the calibration curves each indicate a relationship between the respective hygiene value share of the influencing variable and a further influencing variable, wherein the at least one further influencing variable is kept constant within each calibration curve of the family of curves, wherein the at least one further influencing variable distinguishes between the calibration curves of the family of curves; at least one calibration table, wherein the calibration table respectively indicates a relationship between the respective hygiene value share of the influencing variable and a further influencing variable, wherein the at least one further influencing variable is kept constant; at least one family of calibration tables comprising a plurality of calibration tables, wherein the calibration tables each indicate a relationship between the respective hygiene value share of the influencing variable and a further influencing variable, wherein the at least one further influencing variable is kept constant within each calibration table of the family of tables, wherein the at least one further influencing variable distinguishes between the calibration tables of the family of tables.

Embodiment 11: the method according to one of the preceding embodiments, wherein the method comprises at least one calibration, wherein the relationship between each influencing variable and the respective hygiene value share of said influencing variable is determined during the calibration.

Embodiment 12: the method according to the preceding embodiment, wherein the relationship is stored in at least one data memory after the calibration.

Embodiment 13: the method according to either of the two preceding embodiments, wherein, during the calibration, it is determined how long is required, under respective constant conditions, including prespecified constant values of the influencing variables, until the prespecified desired hygiene value is achieved, in particular a prespecified reduction factor or a prespecified reduction in at least one target germ, wherein the hygiene value share is determined from this information about the time duration, taking into account an initial hygiene value, the desired hygiene value and the time duration.

Embodiment 14: the method according to one of the preceding embodiments, wherein the expected actual hygiene value at the end of the cleaning is determined from the hygiene value shares assuming that the current influencing variables remain unchanged for the rest of the cleaning.

Embodiment 15: the method according to one of the preceding embodiments, wherein the expected actual hygiene value at the end of the cleaning is calculated from the hygiene value shares using at least one algorithm selected from the group consisting of: integration of the sum of the hygiene value shares of the influencing variables over the expected remaining duration of the cleaning; a totality of the Riemann sums with respect to time of the respective hygiene value shares of the influencing variables over the expected remaining duration of the cleaning.

Embodiment 16: the method according to one of the preceding embodiments, wherein the duration of the cleaning is changed when it is identified during the comparison that the expected actual hygiene value differs from the desired hygiene value.

Embodiment 17: the method according to the preceding embodiment, wherein the duration of the cleaning is increased when it is identified that the expected actual hygiene value is lower than the desired hygiene value.

Embodiment 18: the method according to either of the two preceding embodiments, wherein the duration of the cleaning is reduced when it is identified that the expected actual hygiene value is higher than the desired hygiene value.

Embodiment 19: the method according to one of the three preceding embodiments, wherein at least one measure for changing the duration of the cleaning is used, said measure being selected from the group consisting of: at least one program duration of at least one cleaning program is changed; at least one transportation speed of at least one transportation device, by means of which the items to be cleaned are transported through the at least one cleaning chamber, is changed.

Embodiment 20: the method according to one of the preceding embodiments, wherein at least one concentration of at least one additive in the at least one cleaning fluid is changed when it is identified that the expected actual hygiene value differs from the desired hygiene value.

Embodiment 21: the method according to the preceding embodiment, wherein the at least one concentration of the at least one additive in the at least one cleaning fluid is increased when it is identified that the expected actual hygiene value undershoots the desired hygiene value.

Embodiment 22: the method according to either of the two preceding embodiments, wherein the additive comprises at least one substance selected from the group consisting of a detergent concentrate and a disinfectant, in particular chlorine.

Embodiment 23: the method according to one of the preceding embodiments, wherein at least one mechanical application of the at least one cleaning fluid to the items to be cleaned is changed when it is identified during the comparison that the expected actual hygiene value differs from the desired hygiene value.

Embodiment 24: the method according to the preceding embodiment, wherein an intensity of the mechanical application is increased when it is identified that the expected actual hygiene value is lower than the desired hygiene value.

Embodiment 25: the method according to either of the two preceding embodiments, wherein an intensity of the mechanical application is reduced when it is identified that the expected actual hygiene value is higher than the desired hygiene value.

Embodiment 26: the method according to one of the three preceding embodiments, wherein at least one measure for changing the intensity of the mechanical application is used, said measure being selected from the group consisting of: at least one pressure of the at least one cleaning fluid is changed; at least one flow rate of the at least one cleaning fluid is changed.

Embodiment 27: the method according to one of the preceding embodiments wherein, in f., an influencing measure is used for influencing the at least one influencing variable, wherein the influencing measure takes place depending on a prespecified and/or prespecifiable hierarchy of measures.

Embodiment 28: the method according to one of the preceding embodiments, wherein the items to be cleaned are transported through the at least one cleaning chamber by means of at least one transportation device.

Embodiment 29: the method according to the preceding embodiment, wherein the items to be cleaned comprise a plurality of items to be cleaned, wherein each item is allocated a hygienization account in which previous hygienization units to which the items have been subjected are cumulatively stored.

Embodiment 30: the method according to either of the two preceding embodiments, wherein the items to be cleaned comprise a plurality of items to be cleaned, wherein the transportation device is subdivided into sections, wherein each section is allocated a hygienization account in which previous hygienization units to which the items held in the respective section have been subjected are cumulatively stored.

Embodiment 31: the method according to either of the two preceding embodiments, wherein the hygienization account is reset to zero when a fault in the cleaning process is established.

Embodiment 32: the method according to one of the four preceding embodiments, wherein the cleaning chamber is subdivided into a plurality of cleaning zones, wherein each cleaning zone has at least one application device, wherein the items to be cleaned are transported through the cleaning zones by means of the transportation device one after the other.

Embodiment 33: the method according to the preceding embodiment, wherein the method comprises at least one checking step, wherein the checking step is carried out until the items to be cleaned are located within the last cleaning zone in a transportation direction of the transportation device, wherein, during the checking step, the expected actual hygiene value is once again compared with the desired hygiene value and wherein at least one safety measure is taken when the desired hygiene value is undershot.

Embodiment 34: the method according to the preceding embodiment, wherein the safety measure comprises at least one measure selected from the group consisting of: the transportation device is stopped; the transportation device is slowed down; a pressure of the cleaning fluid in the application device of the last cleaning zone is increased; a flow rate of the cleaning fluid in the application device of the last cleaning zone is increased.

Embodiment 35: the method according to either of the two preceding embodiments, wherein the last cleaning zone is a final rinse zone, in particular a fresh water final rinse zone.

Embodiment 36: a cleaning device for cleaning items to be cleaned, comprising at least one cleaning chamber and at least one application device for applying at least one cleaning fluid to the items to be cleaned in the cleaning chamber, wherein the cleaning device further comprises:

I. at least one data memory for storing a prespecification for a desired hygiene value which is to be achieved with the cleaning;

II. at least two measuring devices for time-resolved recording of at least two influencing variables which have an influence on a hygienization of the items to be cleaned;

III. at least one determining device for determining hygiene value shares from the influencing variables using a prespecified relationship between each influencing variable and the respective hygiene value share of said influencing variable;

IV. at least one evaluating device for ascertaining an expected actual hygiene value at the end of the cleaning from the hygiene value shares;

V. at least one comparing device for comparing the expected actual hygiene value with the desired hygiene value; and VI. at least one influencing device for influencing at least one influencing variable depending on the result of the comparison.

Embodiment 37: the cleaning device according to the preceding embodiment, wherein the cleaning device is configured to carry out a method according to one of the preceding embodiments.

Embodiment 38: the cleaning device according to one of the preceding embodiments which relates to a cleaning device, wherein the cleaning device has at least one controller, wherein the data memory, the determining device, the evaluating device, the comparing device and the influencing device are constituent parts of the controller.

Embodiment 39: the cleaning device according to the preceding embodiment, wherein the controller comprises at least one data processing device, in particular at least one processor.

Embodiment 40: the cleaning device according to the preceding embodiment, wherein the data processing device is programmed to allocate in each case one hygiene value share to the influencing variables on the basis of the prespecified relationship and to determine the expected actual hygiene value at the end of the cleaning from the hygiene value shares.

Embodiment 41: the cleaning device according to the preceding embodiment, wherein the data processing device is further programmed to compare the expected actual hygiene value with the desired hygiene value and to identify whether the expected actual hygiene value is lower than the desired hygiene value.

Embodiment 42: the cleaning device according to the preceding embodiment, wherein the data processing device is further programmed to influence the at least one influencing variable depending on the result of the comparison.

Embodiment 43: the cleaning device according to one of the preceding embodiments which relates to a cleaning device, wherein the data memory comprises at least one memory selected from a volatile data memory and a non-volatile data memory.

Embodiment 44: the cleaning device according to one of the preceding embodiments which relates to a cleaning device, wherein the measuring devices comprise at least two sensors selected from the group consisting of: at least one temperature sensor for recording at least one temperature of the at least one cleaning fluid; at least one mechanical or fluidic sensor for recording at least one measurement variable of a mechanical action of the at least one cleaning fluid on the items to be cleaned, in particular at least one pressure sensor for recording at least one pressure of the at least one cleaning fluid and/or at least one flow sensor for recording at least one flow of the at least one cleaning fluid; at least one concentration sensor for recording at least one concentration of at least one disinfectant in the at least one cleaning fluid; at least one concentration sensor for recording at least one concentration of at least one detergent concentrate in the at least one cleaning fluid; at least one pH sensor for recording at least one pH value of the at least one cleaning fluid.

Embodiment 45: the cleaning device according to one of the preceding embodiments which relates to a cleaning device, wherein the cleaning device is selected from the group consisting of a conveyor washer and an automatic programmed washer.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
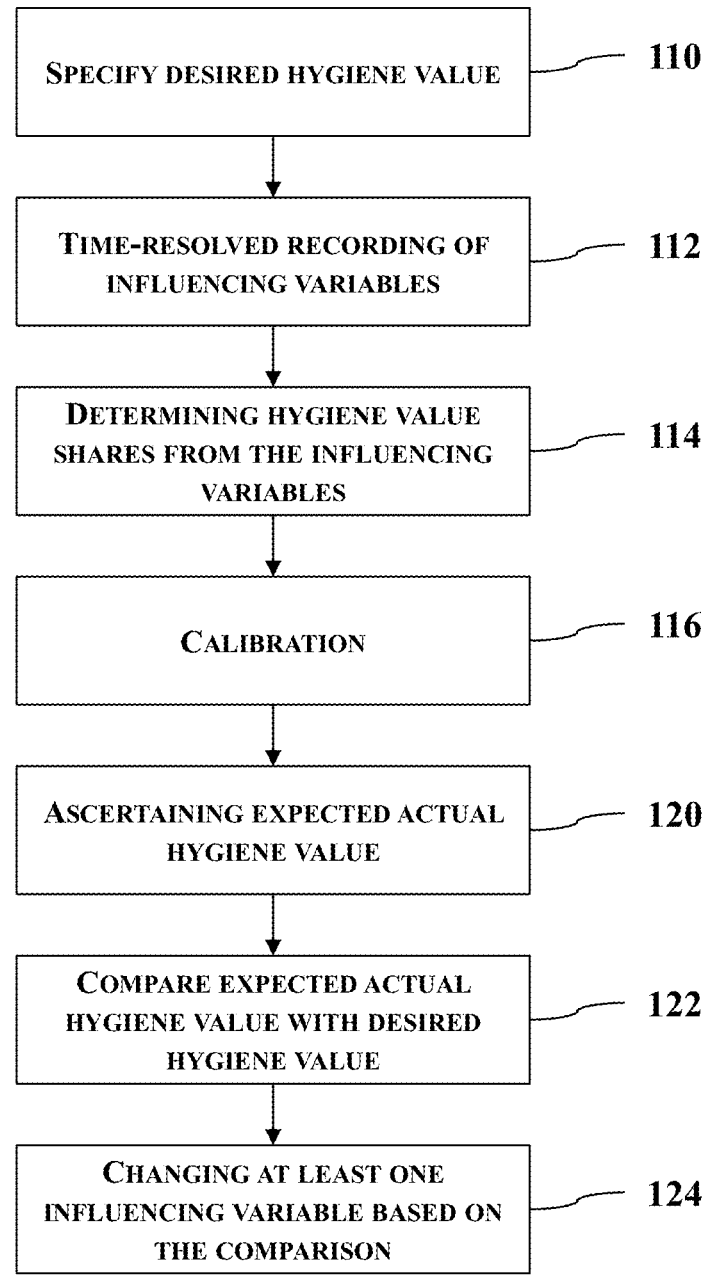
FIG. 1 shows an exemplary embodiment of a method according to this disclosure.

FIG. 1 schematically illustrates an exemplary embodiment of a method according to this disclosure for cleaning items 143 to be cleaned. The method comprises specifying a desired hygiene value 110 which is to be achieved with the cleaning. The desired hygiene value can be selected from the group consisting of: an A0 value according to DIN EN ISO 15883 which is to be achieved overall with the cleaning; a hygiene level according to DIN 10510 which is to be achieved, at the desired prespecifications for tank and boiler temperatures according to DIN 10510; a number of HUE units according to the NSF3 standard which are to be achieved overall with the cleaning; a reduction in a population of a target germ which is to be achieved overall with the cleaning, in particular a reduction in the population of *Staphylococcus aureus* which is to be achieved overall with the cleaning. The desired hygiene value can correspond to 99.999% death of a population of *Staphylococcus aureus*. The hygiene value can preferably be a SUE value. The SUE value per second can be a measure of the reduction in the target germ, which measure takes into account the dependency on the temperature and the detergent chemicals used, where $$\text{SUE/sec} = Ae^{BT},$$

where $A=1/7000000$ and $B=0.191$. Here, a SUE value of 100 corresponds to a 5 log-level reduction in the target germ. The parameters A and B are empirical values determined using a population of *Staphylococcus aureus* as target germ population. For example, the prespecification of the desired hygiene value 110 which is to be achieved with the cleaning can comprise selecting a desired hygiene value from a list and/or entering a desired hygiene value, for example into a man/machine interface of the cleaning device 126, in particular of a controller 118 of the cleaning device 126.

The method comprises time-resolved recording of at least two influencing variables 112 which have an influence on a hygienization of the items 143 to be cleaned. The influencing variables can be selected from the group consisting of: a duration of the cleaning; at least one temperature of the at least one cleaning fluid; at least one measurement variable which is characteristic of a mechanical action of the at least one cleaning fluid on the items 143 to be cleaned, in particular a pressure and/or a flow rate of the at least one cleaning fluid; at least one concentration of at least one disinfectant in the at least one cleaning fluid; at least one concentration of at least one detergent concentrate in the at least one cleaning fluid; at least one pH value of the at least one cleaning fluid; at least one measurement variable which is characteristic of an effect of a final rinse operation. The influencing variables can influence each other. A reduction in one of these influencing variables can respectively be compensated for by increasing one or more of the other influencing variables. The at least two influencing variables can comprise, as first influencing variable, at least one temperature of the at least one cleaning fluid and furthermore at least one further influencing variable.

The method comprises determining hygiene value shares from the influencing variables 114 using a prespecified relationship between each influencing variable and the respective hygiene value share of said influencing variable. The relationship between the influencing variables and the respective hygiene value shares of said influencing variables can be prespecified by at least one of the following prespecifications: at least one calibration curve, in particular at least one curve relating to a hygiene effect, wherein the calibration curve respectively indicates a relationship between the respective hygiene value share of the influencing variable and a further influencing variable, wherein the at least one further influencing variable is kept constant; at least one family of curves comprising a plurality of calibration curves, wherein the calibration curves each indicate a relationship between the respective hygiene value share of the influencing variable and a further influencing variable, wherein the at least one further influencing variable is kept constant within each calibration curve of the family of curves, wherein the at least one further influencing variable distinguishes between the calibration curves of the family of curves; at least one calibration table, wherein the calibration table respectively indicates a relationship between the respective hygiene value share of the influencing variable and a further influencing variable, wherein the at least one further influencing variable is kept constant; at least one family of calibration tables comprising a plurality of calibration tables, wherein the calibration tables each indicate a relationship between the respective hygiene value share of the influencing variable and a further influencing variable, wherein the at least one further influencing variable is kept constant within each calibration table of the family of tables, wherein the at least one further influencing variable distinguishes between the calibration tables of the family of tables. In this way, a dependency of the individual influencing variables in relation to one another can be determined. When taking into account at least two influencing variables, in particular all influencing variables, a multidimensional field can be determined, in which multidimensional field the individual influencing variables can be varied.

The method can comprise at least one calibration 116 in which the relationship between each influencing variable and the respective hygiene value share of said influencing variable can be determined. For example, the calibration 116 can take place once, for example at first start-up. For example, the calibration 116 can take place repeatedly, for example at prespecifiable or selectable time intervals. The relationship can be stored in at least one data memory, for example of a controller 118, after the calibration 116. For example, the relationship can be stored in a table, wherein, for example, the calibration curves are stored as discrete values. During the calibration 116, it is possible to determine how long is required, under respective constant conditions, including prespecified constant values of the influencing variables, until the prespecified desired hygiene value is achieved, in particular a prespecified reduction factor or a prespecified reduction in at least one target germ, wherein the hygiene value share is determined from this information about the time duration, taking into account an initial hygiene value, the desired hygiene value and the time duration.

The method comprises ascertaining an expected actual hygiene value at the end of the cleaning from the hygiene value shares 120. Ascertaining the expected actual hygiene value 120 can comprise taking into account and/or adding up all previously achieved hygiene value shares, that is to say hygiene value shares achieved up to the time at which the expected actual hygiene value 120 is ascertained. In particular, all hygiene value shares acting on the items 143 to be cleaned since a start time of a cleaning program can be taken into account and/or added up. The expected actual hygiene value can be a prediction of the actual hygiene value at the end of the cleaning. The expected actual hygiene value at the end of the cleaning can be determined from the hygiene value shares assuming that the current influencing variables remain unchanged for the rest of the cleaning. The expected actual hygiene value at the end of the cleaning can be calculated from the hygiene value shares using at least one algorithm selected from the group consisting of: integration of the sum of the hygiene value shares of the influencing variables over the expected remaining duration of the cleaning; a totality of the Riemann sums with respect to time of the respective hygiene value shares of the influencing variables over the expected remaining duration of the cleaning.

The method comprises comparing the expected actual hygiene value with the desired hygiene value 122. The comparison 122 can comprise determining overshooting and/or undershooting of the expected actual hygiene value and the desired hygiene value. The comparison 122 can comprise a mathematical comparison. In particular, the comparison 122 can comprise identifying whether the expected actual hygiene value is lower than the desired hygiene value. The method comprises influencing or changing at least one influencing variable 124 depending on the result of the comparison. Influencing of the at least one influencing variable 124 can take place at prespecified or prespecifiable times.

Figure 2:
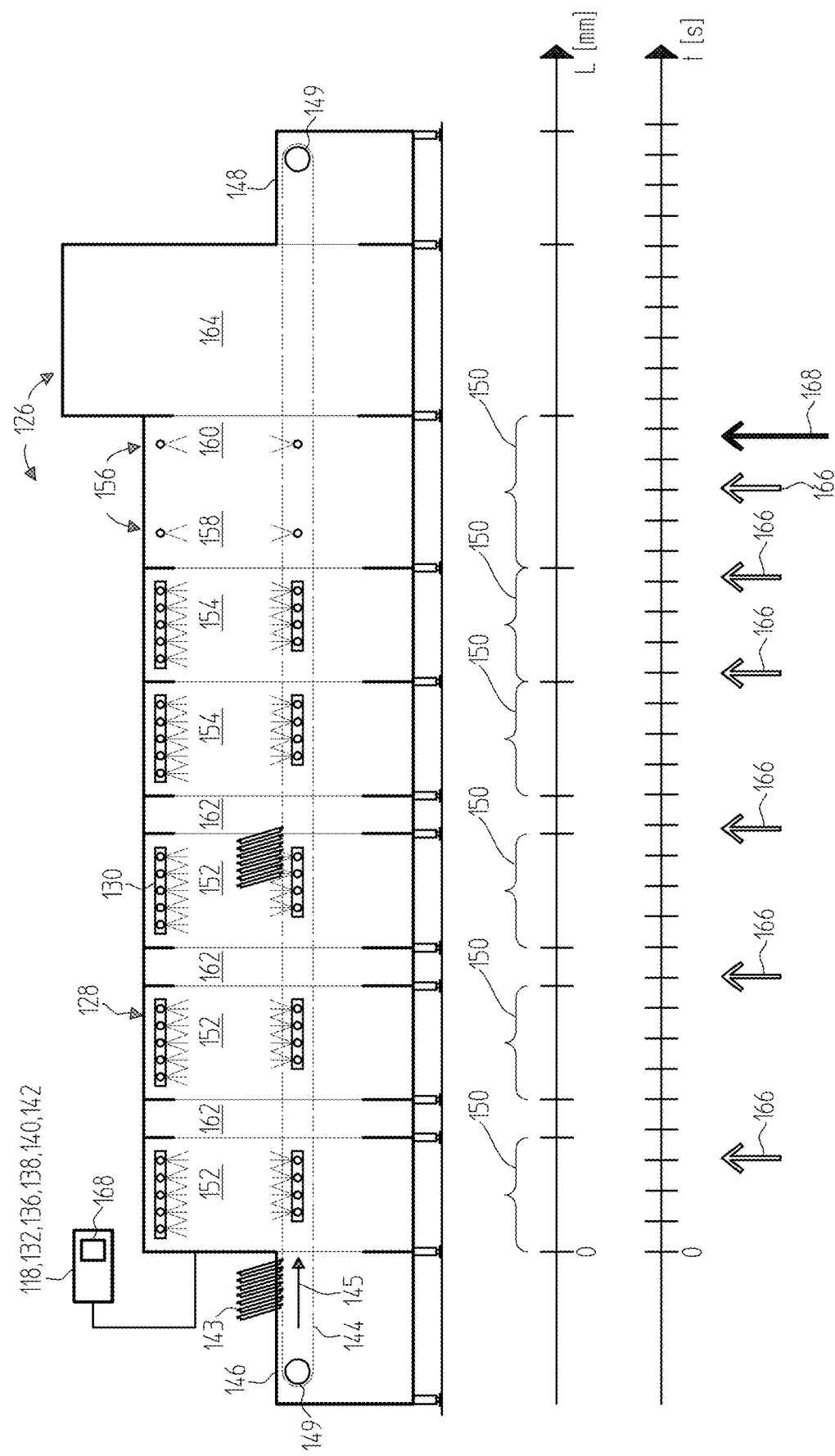
FIG. 2 shows an exemplary embodiment of a cleaning device according to this disclosure.

FIG. 2 shows a schematic illustration of an embodiment of a cleaning device 126 having at least one cleaning chamber 128 and at least one application device 130 for applying at least one cleaning fluid to the items 143 to be cleaned in the cleaning chamber 128. The cleaning device 126 comprises at least one data memory 132 for storing a prespecification for a desired hygiene value which is to be achieved with the cleaning, at least two measuring devices 134, not illustrated in FIG. 2, for time-resolved recording of at least two influencing variables which have an influence on a hygienization of the items 143 to be cleaned, at least one determining device 136 for determining hygiene value shares from the influencing variables using a prespecified relationship between each influencing variable and the respective hygiene value share of said influencing variable, at least one evaluating device 138 for ascertaining an expected actual hygiene value at the end of the cleaning from the hygiene value shares, at least one comparing device 140 for comparing the expected actual hygiene value with the desired hygiene value, and at least one influencing device 142 for influencing at least one influencing variable depending on the result of the comparison. The data memory 132, the determining device 136, the evaluating device 138, the comparing device 140 and the influencing device 142 can be constituent parts of the controller 118.

In the exemplary embodiment illustrated in FIG. 2, the items 143 to be cleaned, for example in the form of dishes, can be conveyed through the cleaning chamber 128, for example in the form of a tunnel, by means of at least one transportation device 144 in the transportation direction 145. In FIG. 2, the transportation direction 145 is identified by an arrow. To this end, the cleaning device 126 can be configured, for example, as a flight-type conveyor or as a rack conveyor. For example, at least one inlet 146, at which the items 143 to be cleaned are passed to the transportation device 144, and at least one outlet 148, at which the cleaned items 143 can be removed, can be provided. The transportation device 144 can accordingly comprise, for example, a conveyor belt. Other refinements are also possible. The transportation device 144 can comprise, for example, at least one drive 149.

The cleaning chamber 128 can be subdivided into a plurality of cleaning zones 150. In the cleaning zones 150, cleaning fluid can be applied to the items 143 to be cleaned by means of the application device 130, for example a fluid devices. Each cleaning zone 150 can have at least one application device 130. For example, at least one nozzle system, not illustrated in FIG. 2, can be provided for this purpose, which nozzle system can be fed with cleaning fluid from a tank for example by means of a pump, not illustrated in FIG. 2, and a line system, not illustrated. The items 143 to be cleaned can be transported through the cleaning zones 150 one after the other by means of the transportation device 144. In FIG. 2, the transportation path L and the length of the cleaning zones 150 are shown in mm.

In the embodiment shown in FIG. 2, the cleaning device 126 can have, for example, a plurality of wash tanks 152 in which at least one cleaning fluid is applied to the items 143 to be cleaned at a temperature. For example, a wash zone nozzle system, not illustrated, can be provided in the wash tanks 152, the so-called wash zone, which wash zone nozzle system can be fed with cleaning fluid from a washing tank, for example, by means of a pump, likewise not illustrated, and a line system, likewise not illustrated. Furthermore, the cleaning device 126 can have one or more thermal disinfection zones 154 which are configured to carry out thermal disinfection. The cleaning device 126 can have at least one final rinse zone 156 which is subdivided, for example, into a pump final rinse arrangement 158 and a fresh water final rinse arrangement 160. For example, a rinse nozzle system can be provided in the final rinse zone 158 and 160, which rinse nozzle system can be fed with heated fresh water and/or with rinsing fluid from a rinse tank. The pump final rinse arrangement 158 can be configured to carry out at least one final rinse cycle in a recirculation method using at least one final rinse liquid. In the fresh water final rinse arrangement 160, fresh water, which can optionally be heated and/or admixed with a final rinse aid, in particular as a so-called final rinse solution, can be applied to the items 143 to be cleaned by means of the application device 130 and therefore final residues of soiling and residues of the cleaning fluid are rinsed off from the items 143 to be cleaned. The cleaning device 126 can further have one or more neutral zones 162 in which no cleaning takes place. After passing through the cleaning zones 150, the items 143 to be cleaned can then enter at least one drying zone 164 in which hot air can be applied to the items 143 to be cleaned for example by means of a fan in order to accelerate drying of the items 143 to be cleaned.

Determining hygiene value shares from the influencing variables using a prespecified relationship between each influencing variable and the respective hygiene value share 120 of said influencing variable and adding up previously achieved hygiene value shares can take place at different times during the transportation of the items 143 to be cleaned through the cleaning chamber 128. A time axis t with time units is shown in FIG. 2. Exemplary times at which determining of hygiene value shares 120 and adding up of the determined hygiene value shares can take place are identified in FIG. 2 as arrows with reference numeral 166. In particular, display of the previously achieved hygiene values can take place at these times 166, for example on a display device 168, in particular a display, of the controller 118. The determining device 136 is configured to determine hygiene value shares from the influencing variables using the prespecified relationship between each influencing variable and the respective hygiene value share of said influencing variable. For recording the influencing variable, the cleaning device 126 has at least two measuring devices 134, not illustrated in FIG. 2, which are configured to detect at least one influencing variable in a time-resolved manner. The measuring devices 134 can comprise at least two sensors selected from the group consisting of: at least one temperature sensor for recording at least one temperature of the at least one cleaning fluid; at least one mechanical or fluidic sensor for recording at least one measurement variable of a mechanical action of the at least one cleaning fluid on the items 143 to be cleaned, in particular at least one pressure sensor for recording at least one pressure of the at least one cleaning fluid and/or at least one flow sensor for recording at least one flow of the at least one cleaning fluid; at least one concentration sensor for recording at least one concentration of at least one disinfectant in the at least one cleaning fluid; at least one concentration sensor for recording at least one concentration of at least one detergent concentrate in the at least one cleaning fluid; at least one pH sensor for recording at least one pH value of the at least one cleaning fluid.

At times 166, the expected actual hygiene value can be compared with the desired hygiene value and influencing of at least one influencing variable can take place if the desired hygiene value is undershot. For example, a duration of the cleaning and/or a mechanical effect and/or an effect of the final rinse arrangement and/or a concentration and/or metering and/or at least one pH value and/or the temperature of the at least one cleaning fluid can be increased in at least one cleaning zone that follows in the transportation direction.

The cleaning device 126 can be configured to carry out at least one checking step. The checking step can be carried out until the items 143 to be cleaned are located within a last cleaning zone, for example the final rinse zone 156, in particular the fresh water final rinse zone 160, in a transportation direction. For example, the checking step can take place at a time identified by arrow and reference numeral 168. During the checking step, the expected actual hygiene value can once again be compared with the desired hygiene value and at least one safety measure can be taken when the desired hygiene value is undershot. The safety measure can comprise at least one measure selected from the group consisting of: the transportation device 145 is stopped; the transportation device 145 is slowed down; a pressure of the cleaning fluid in the application device 130 of the last cleaning zone 160 is increased; a flow rate of the cleaning fluid in the application device 130 of the last cleaning zone 160 is increased.

Figure 3:
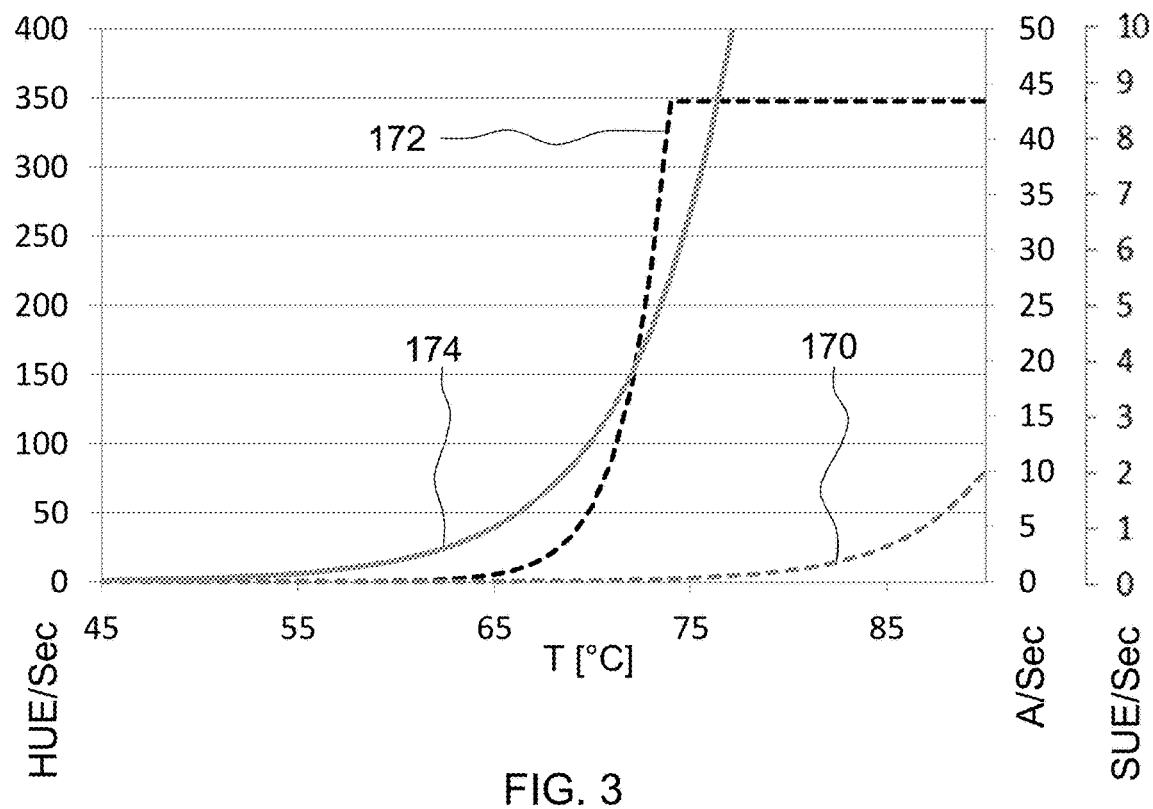
FIG. 3 shows a comparison of the achieved hygiene value shares per second according to A0 methods, according to HUE methods and according to SUE methods.

FIG. 3 shows a comparison of the achieved hygiene value shares per second according to A0 methods (identified by reference numeral 170), according to HUE methods (identified by reference numeral 172) and according to the SUE method (identified by reference numeral 174) for a concentration (2.5 ml/l surfactant+2.5 ml/l potassium hydroxide). The HUE value per second is plotted from 0 to 400 on the left-hand-side Y axis and the A0 value per second is plotted from 0 to 50 on a first right-hand-side Y axis and the SUE per second is plotted from 0 to 10 on a second right-hand-side Y axis. All curves show a high temperature dependency. However, A0 methods and HUE methods do not take into account the influence of the concentration or composition of the at least one additive of the cleaning fluid on the hygiene effect. For example, high temperatures may be required in order to achieve a hygiene level prespecified according to A0 or HUE methods. The SUE method can allow the concentration or composition of the at least one additive of the cleaning fluid on the hygiene effect to be taken into account and therefore render possible operation of the cleaning device at low temperatures with the hygiene effect remaining the same.

Figure 4:
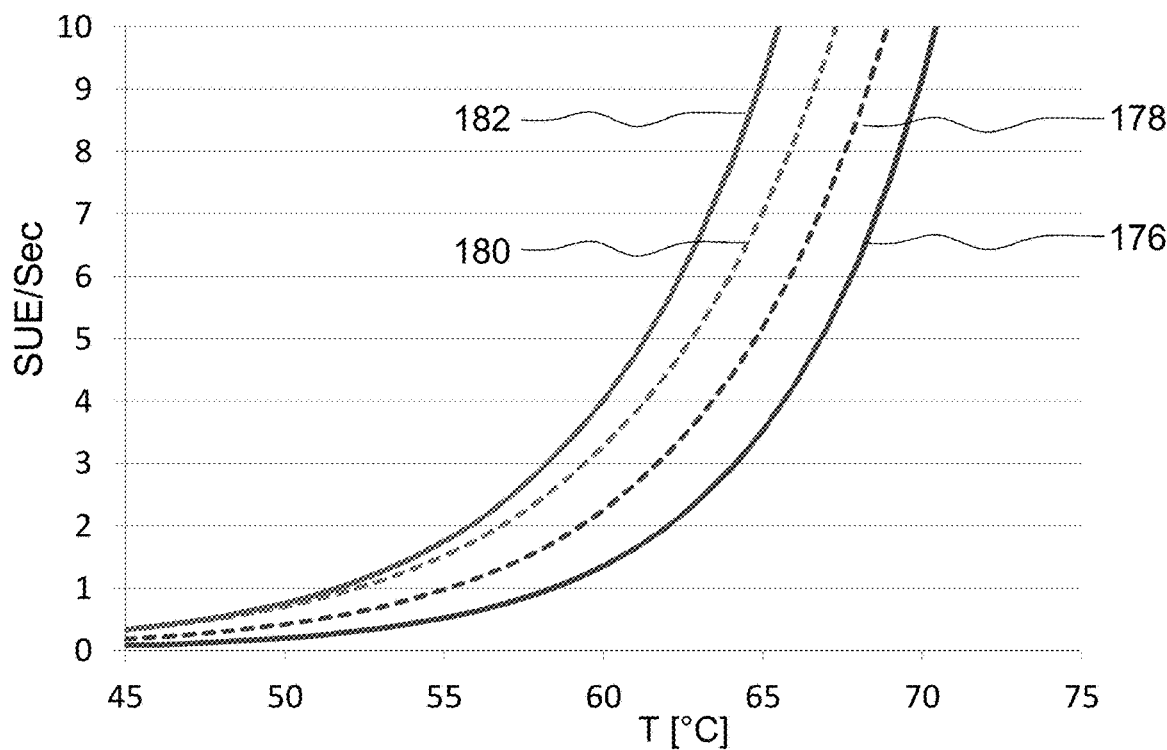
FIG. 4 shows a prespecified relationship between the influencing variable temperature, the hygiene value share of said influencing variable according to the SUE method and the concentration.

FIG. 4 shows a prespecified relationship between the influencing variable temperature T in ° C., the hygiene value share of said influencing variable according to the SUE method and the concentration. Curve 176 shows the influence of the temperature for a concentration of (2.5 ml/l surfactant+2.5 ml/l potassium hydroxide). Curve 178 shows the influence of the temperature for a concentration of (5 ml/l surfactant+5 ml/l potassium hydroxide). Curve 180 shows the influence of the temperature for a concentration of (7.5 ml/l surfactant+7.5 ml/l potassium hydroxide). Curve 182 shows the influence of the temperature for a concentration of (10 ml/l surfactant+10 ml/l potassium hydroxide). By increasing the concentration, a higher hygienization value share can be achieved with the temperature remaining the same. An increase in the concentration can therefore compensate for a drop in temperature.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE SYMBOLS

110 Prespecifying a desired hygiene value which is to be achieved with the cleaning
112 Time-resolved recording of at least two influencing variables
114 Determining hygiene value shares from the influencing variables
116 Calibration
118 Controller
120 Ascertaining an expected actual hygiene value at the end of the cleaning from the hygiene value shares
122 Comparing the expected actual hygiene value with the desired hygiene value
124 Influencing at least one influencing variable
126 Cleaning device
128 Cleaning chamber
130 Application device
132 Data memory
134 Measuring devices
136 Determining device
138 Evaluating device
140 Comparing device
142 Influencing device
143 Items to be cleaned
144 Transportation device
145 Transportation direction
146 Inlet
148 Outlet
149 Drive
150 Cleaning zones
152 Wash tank
154 Thermal disinfection zone
156 Final rinse zone
158 Pump final rinse arrangement
160 Fresh water final rinse arrangement
162 Neutral zones
164 Drying zone
166 Time
168 Time
170 Hygiene value shares per second according to A0 methods
172 Hygiene value shares per second according to HUE methods
174 Hygiene value shares per second according to SUE methods
176 Curve
178 Curve
180 Curve
182 Curve

What is claimed is:

1. A method for controlling a process for cleaning items to be cleaned, comprising:
    (a) using a cleaning device having at least one cleaning chamber and at least one applicator for applying at least one cleaning fluid to the items to be cleaned in the cleaning chamber;
    (b) specifying a desired overall hygiene value for the items to be cleaned;
    (c) time-resolved recording of first and second influencing variables which influence hygienization of the items to be cleaned;
    (d) using a first calibration to derive a first hygiene value share from the first influencing variable and using a second calibration to derive a second hygiene value share from the second influencing variable;
    (e) combining the first and second hygiene value shares to determine an expected overall hygiene value at the end of the cleaning;
    (f) comparing the expected overall hygiene value with the desired overall hygiene value; and
    (g) changing at least one of the first and second influencing variables based on the comparison.

2. The method as claimed in claim 1, wherein step (f) further comprises identifying whether the expected overall hygiene value is lower than the desired overall hygiene value.

3. The method as claimed in claim 1, wherein the desired overall hygiene value is selected from the group consisting of: an A0 value; a hygiene level to be achieved at specifications for tank and boiler temperatures; a number of HUE units; a reduction in a population of a target germ.

4. The method as claimed in claim 1, wherein the first and second influencing variables are different and are selected from the group consisting of: a duration of the cleaning; at least one temperature of the at least one cleaning fluid; at least one measurement variable which is characteristic of a mechanical action of the at least one cleaning fluid on the items to be cleaned; at least one concentration of at least one disinfectant in the at least one cleaning fluid; at least one concentration of at least one detergent concentrate in the at least one cleaning fluid; at least one pH value of the at least one cleaning fluid; at least one measurement variable which is characteristic of an effect of a final rinse operation.

5. The method as claimed in claim 1, wherein one of the two influencing variables is the temperature of the at least one cleaning fluid.

6. The method as claimed in claim 1, wherein the first calibration is selected from the group consisting of:

using a calibration curve that indicates a relationship between the first hygiene value share and the second influencing variable, wherein the second influencing variable is kept constant;

using a family of curves comprising a plurality of calibration curves, wherein the calibration curves each indicate a relationship between the first hygiene value share and the second influencing variable, wherein the second influencing variable is kept constant within each calibration curve of the family of curves, wherein the second influencing variable distinguishes between the calibration curves of the family of curves;

using a calibration table that indicates a relationship between the first hygiene value share and the second influencing variable, wherein the second influencing variable is kept constant;

using a family of calibration tables comprising a plurality of calibration tables, wherein the calibration tables each indicate a relationship between the first hygiene value share and the second influencing variable, wherein the second influencing variable is kept constant within each calibration table of the family of tables, wherein the second influencing variable distinguishes between the calibration tables of the family of tables.

7. The method as claimed in claim 1, wherein when the comparison of step (f) indicates that the expected overall hygiene value differs from the desired overall hygiene value, changing:
the duration of the cleaning;
at least one concentration of at least one additive in the at least one cleaning fluid; and/or
at least one mechanical application of the at least one cleaning fluid.

8. The method as claimed in claim 1, wherein the items to be cleaned comprise a plurality of items to be cleaned, wherein each item is allocated a hygienization account in which previous hygienization units to which the item has been subjected are cumulatively stored.

9. The method as claimed in claim 1, wherein the items to be cleaned are transported through the at least one cleaning chamber by a transporter that is subdivided into sections, each section being allocated a hygienization account in which previous hygienization units to which the items held in the respective section have been subjected are cumulatively stored.

10. The method of claim 1, wherein step (d) comprises:
maintaining the second influencing variable constant while using the first calibration to derive the first hygiene value share; and
maintaining the first influencing variable constant while using the second calibration to derive the second hygiene value share.

11. The method of claim 1, wherein step (e) comprises using an integration or Riemann sum algorithm to combine the first and second influencing variable shares.

12. The method as claimed in claim 3, wherein the desired overall hygiene value is a reduction in a population of a target germ to be achieved with the cleaning, wherein the target germ is *Staphylococcus aureus*.

13. The method as claimed in claim 4, wherein the first influencing variable is at least one measurement variable which is characteristic of a mechanical action of the at least one cleaning fluid on the items to be cleaned, wherein the measurement variable is one or both of a pressure or a flow rate of the at least one cleaning fluid.

14. The method as claimed in claim 6, comprising using a calibration curve relating to a hygiene effect.

15. The method as claimed in claim 7, wherein at least one measure for changing the intensity of the mechanical application is used, said measure being selected from the group consisting of: at least one pressure of the at least one cleaning fluid is changed; at least one flow rate of the at least one cleaning fluid is changed.

16. The method as claimed in claim 9, further comprising at least one checking step carried out until the items to be cleaned are located within the last cleaning zone in a transportation direction of the transporter, wherein, during the at least one checking step, the expected overall hygiene value is again compared with the desired overall hygiene value, and wherein at least one safety measure is taken when the desired hygiene value is undershot.

* * * * *